United States Patent [19]
Andon et al.

[11] Patent Number: 6,080,431
[45] Date of Patent: *Jun. 27, 2000

[54] COMBINED CALCIUM AND VITAMIN SUPPLEMENTS FOR BONE GROWTH

[75] Inventors: Mark Benson Andon, Fairfield; Kenneth Thomas Smith, Cincinnati, both of Ohio

[73] Assignee: The Procter & Gamble Company, Cincinnati, Ohio

[*] Notice: This patent is subject to a terminal disclaimer.

[21] Appl. No.: 08/369,555

[22] Filed: Jan. 6, 1995

Related U.S. Application Data

[63] Continuation of application No. 08/108,151, Aug. 17, 1993, abandoned, which is a continuation of application No. 07/944,024, Sep. 11, 1992, abandoned, which is a continuation of application No. 07/695,823, May 6, 1991, abandoned.

[51] Int. Cl.$^7$ .......................... A61K 31/59; A61K 33/42
[52] U.S. Cl. ............................. 424/602; 516/167
[58] Field of Search ............................. 552/653; 514/168, 514/167, 602; 424/630, 638, 641

[56] References Cited

U.S. PATENT DOCUMENTS

| | | | |
|---|---|---|---|
| 3,949,098 | 4/1976 | Bangert | 426/324 |
| 3,950,547 | 4/1976 | Lamar et al. | 426/74 |
| 3,992,555 | 11/1976 | Kovacs | 426/72 |
| 4,070,488 | 1/1978 | Davis | 426/72 |
| 4,107,346 | 8/1978 | Kravitz | 426/648 |
| 4,214,996 | 7/1980 | Buddemeyer et al. | 252/1 |
| 4,229,358 | 10/1980 | De Luca et al. | 552/653 |
| 4,351,735 | 9/1982 | Buddemeyer et al. | 252/1 |
| 4,419,369 | 12/1983 | Nichols et al. | 426/2 |
| 4,497,800 | 2/1985 | Larson et al. | 514/2 |
| 4,551,342 | 11/1985 | Nakel et al. | 426/548 |
| 4,722,847 | 2/1988 | Heckert | 426/74 |
| 4,737,375 | 4/1988 | Nakel et al. | 426/590 |
| 4,830,862 | 5/1989 | Braun et al. | 426/74 |
| 5,151,274 | 9/1992 | Saltman et la. | 424/630 |

FOREIGN PATENT DOCUMENTS

| | | |
|---|---|---|
| 0304987 | of 1989 | European Pat. Off. . |
| 0297681 | 4/1989 | European Pat. Off. . |
| 0343703 | 11/1989 | European Pat. Off. . |
| 2 845 570 | 4/1980 | Germany . |
| 2845570 | 4/1980 | Germany . |
| 56/097248 | of 1981 | Japan . |
| 56/097248 | 8/1981 | Japan . |
| 9202235 | 2/1992 | WIPO . |
| WO 9202235 | 2/1992 | WIPO .................. 424/630 |
| 96/31130 | 10/1996 | WIPO . |
| WO 9631130 | 10/1996 | WIPO .................. A23L 1/303 |

OTHER PUBLICATIONS

CA: 113(15)1310026—(Kochanowski) (1990).
CA: 113(25)230023r—(Mueller et al) (1990).
Dawson—Hughes et al, A Controlled Trial of the Effect of Calcium Supplementation on Bone Density in Postmenopausal Women., New England Journal of Medicine, vol. 323(13) pp. 878–883 (1990).
Guthrie, Helen Andrews, "Introductory Nutrition", The C. V. Mosby Company, 1971 pp. 123–124; pp. 203–206.
H. Spencer et al., "NIH Concensus Conference: Osteoporosis", Journal of Nutrition, 116, pp. 316–319 (1986).
W.A. Peck et al., Physician's Resource Manual on Osteoporisis, National Osteoporatic Foundation (1987).
Hughes et al., Effects of Calcium Carbonate and Hydroxyapatite on zinc and iron retention in postmenopausal women, American Journal of Clinical Nutrition,: Jul. 1986, pp. 83–88.
S. V. Ting, "Nutrients and Nutrition of Citrus Fruits", ACS 1980.
Hungerford et al., "Interactions of pH and Ascorbate in Intestinal Iron Absorption" American Institute of Nutrition, 1983, pp. 2615–2622.
Riis et al., "Does calcium supplementation prevent postmenopausal bone loss?", New England Journal of Medicine, 316, pp. 173–177 (1987).
L. Nilas et al., "Calcium Supplementation and Postmenopausal bone loss", British Medical Journal, 289, pp. 1103–1106 (1984).
Whedon et al., Current advances in skeletogenisis, Elsevier, (1985).
Hayes et al., Pharmacological basis of therapeutics, 7th Ed., Chapter 65 (1985).
Rao et al., J. Chem. Endo. Metab., 67, pp. 1294–1298 (1988).
Lukert, Calcif. Tissue Int., 40, pp. 119–125 (1987).
B.L. Riggs et al., Physician's Resource Manual on Osteoporosis, National Osteoporatic Foundation (1991).
Dawson–Hughes, Dr. B., Effect of vitamin D Supplementation on wintertime and overall bone loss in healthy postmenopausal women, Annuals of Internal Medicine, vol. 115, pp. 505–512, 1991.
Holbrook et al., Lancet, 5, pp. 1046–1049 (Nov. 5, 1988).
Nordin et al., Brit. Med. Journal, 16, pp. 451–454 (Feb. 16, 1980).
Orwoll et al., Ann. of Internal Medicine, 112(1), pp. 29–34 (Jan. 1, 1990).
Clayman, ed., Encyclopedia of Medicine, Am. Medical Assoc., Vitamin D, 1059 (1989).
Stedman's Medical Dictionary, 25th ed., Williams & Wilkins, v.D., 1726, (1990).
Reynolds et al., Martindale The Extra Pharmacopeia, 28th ed., Pharmaceutical Press., pp. 1657–1659 (1982).
Japanses Patent Abstracts, vol. 13, No. 532 (C 659) (Nov. 1989).

(List continued on next page.)

*Primary Examiner*—Theodore J. Criares
*Attorney, Agent, or Firm*—Rose Ann Dabek; Karen F. Clark

[57] ABSTRACT

Nutritional mineral supplements comprising calcium citrate malate and vitamin D are disclosed. Estrogen can also be used with these supplements. These supplements, which provide at least 25% RDA of calcium and vitamin D are used in addition to the normal diet. These supplements are useful for increasing bone growth and for treating age-related bone loss in humans and animals.

28 Claims, No Drawings

OTHER PUBLICATIONS

Kopitzki et al., Dietary Calcium and bone structure, Ernahrungs–Umschau, vol. 38, No. 5, 1991, pp. 186–191 (with English translation).

Detlef J. G. Muller et al., "Calcium–Citrate–Malate (CCM): An Alternative Calcium Source", Ernahrungs–Umschau, vol. 37, No. 5, 1990, pp. 209–212; Translation.

Christiansen, D. et al. "Effect of 1,25–dihydroxy–vitamin D3 in itself or combined with hormone treatment in preventing postmenopausal osteoporosis"; European Journal of Clinical Investigation (1981) 11, pp. 305–309.

Ott, S. M. et al. "Calcitriol Treatment is not Effective in Postmenopausal Osteoporosis", Annals of Internal Medicine; (Feb. 15, 1989); vol. 110, No. 4; pp. 267–274.

Guthrie, "Introductory Nutrition", The C.V. Mosby Co., St. Louis, 1971, 2nd Ed. pp. 123–124 and 203–206.

Haynes, et al., Pharmacological Basis of Therapeutics, 7th Ed., Chapter 65 (1985).

Bowen, Charles and Peyton, David, "How to Get the Most out of Compuserve," Second Edition, Bantam Computer Books (Feb. 1996).

To, C.K. et al., "Knowledge Engineering Approach to Data Centres Disaster Backup/Recovery Planning," Dept. of Computing Studies Hong Kong Polytechnic, Kowloon, Hong Kong, pp. 241–248, 1989 IEEE.

Arneson, David A., "Mass Storage Archiving in Network Environments," Control Data Corporation, Arden Hills, Minnesota, pp. 45–50 (1988 IEEE).

Ford, Ric, et al., "Juggling Features and Options in Retrospect," *MacWeek,* V5, N10, p. 52 (Mar. 12, 1991).

Steinberg, Jeffrey A., "Diverting Data from Disaster (Advanced Systems Concepts Inc.'s Remote Shadow Option Disk Shadowing Software)," *Software Review (Evaluation),* Abstract.

S. Armbrust et al., *PC Tech Journal,* vol. 3, No. 9, "Forward Looking VDI," Sep. 1985, pp. 52–53.

E.R. Carpenter, *IBM Technical Disclosure Bulletin,* vol. 34, No. 10B, "single System Imagewith Network File Systems," IBM Corp., Mar. 1992, pp. 408–409.

M. Tabes, *Datamation,* "Managing Storage Across the Enterprise," May 1992, pp. 36–40.

P. Korzeniowski, *Software Magazine,* "Back to the Mainframe for Storage of LAN Data," Jul. 1992, pp. 73–77.

Mark Ludwig, *The Little Black Book of Computer Viruses,* American Eagle publications, 1991, pp. 11–19, 23–29, 55–68, 69–76, 159–162.

R. Waterman, *Software Magazine,* "Waiting for X500," Jul. 1992, 2 pages.

R. Brown, *Systems 3X/400,* "Serving Many Masters," Mar. 1992, pp. 68–70.

*PC Computing,* "Test and Evaluation Methods," Jun. 1992, pp. 238, 240, 247–248 and 262.

Price List, "Tape Backup," 1 page.

Advertisement, "Let's Talk®, Tired of the Runaround?," 1 page.

Advertisement, "PC/TCP® Plus," 1 page.

Advertisement, News 3X/400, "Mimix Hi–Net, Lakeview Technology Inc.," Sep. 1991, p. 140.

Advertisement, Network Innovation, "Server Based Backup," 1 page.

Advertisement, News 3X/400, "PC File Mail," Nov. 1991, p. 74.

Advertisement, "Hands On Software, Monarch 36/400 lets PC users get their hands on mid–range data," 1 page.

Advertisement, Andrew, "NetLynx: LAN Connectivity by the Numbers," 1 page.

Advertisement, "Innovation® Data Processing, FDR. Your DASD Management System," 1 page.

Advertisement, "Maynard®, Maynard Delivers a Super Bundle," 1 page.

Advertisement, "Central Point Software, Inc.®, Never Underestimate the Importance of Complete Protection," 1 page.

Advertisement, Business Communications, Gazelle, "Backup While You Work," Jun. 1992, p. 436.

Advertisement, "Works," 1 page.

Advertisement, Intel®, Introducing fax software that can send, receive and run with your faxes, 1 page.

Advertisement, "LapLink, With LapLink you're only a phone call away," 1 page.

M. Tischer, PC Systems Programming, Abacus, Apr. 1993, pp. 157–171, 208–12, Appendix B and C.

Advertisement, PC/Computing, "SequelLink, MiddleWare: Open Windows for Client/Server Computing," p. 427.

Advertisement, System Software Associates, Inc., BPCS Client/Server Application Software, 1 page.

Advertisement, "Rochester Software Connection, Inc., What's fast, fun and does the AS/400?" 1 page.

Robert Jourdan, *Programers Problem Solver,* Prentice Hall, 1996, pp. 369–394, 395–406.

The Waite Group, *MS–DOS Developers Guide,* Howard Sams & Co., 1989, pp. 281–354, 583, 739–748.

Advertisement, PC/Computing, Control up to 96 PC file servers with 1 keyboard and monitor using . . . Commander by cybex, p. 433.

G. Campbell & J. Heim, *PC World,* "The Best of Online Services," Oct. 1993, pp. 225–240.

C. Shipley, *Personal Computing,* Ziff–Savis, "The World at Your Fingertips," Fall 1993, pp. 52–56.

J. Burgess, *Washington Post Business Magazine Monday Section,* Wash Tech, Cybertalk, "Avoiding Highway Robbert," Nov. 1993, pp. 19, 26.

K. Neely, *Midrange Computing,* "Terminal Emulator or Network: A Management Guide," Sep. 1993, pp. 56–60.

P. Borsook, *InfoWorld,* "Enterprise Computing, Internetworking," Feb. 1, 1993, pp. 48–49.

F. Derfler & S. Rigney, *PC Manazine,* vol. 10, No. 15, "From LAN to WAN, Bringing Your Networks Together," Sep. 10, 1991, pp. 106–118.

F. Derfler & S. Rigney, *PC Magazine,* vol. 10, No. 15, "Bridges and Routers, Smart Links Between LAN Segments," Sep. 10, 1991, p. 121–169.

M. Thompson & S. Rigney, *PC Magazine,* vol. 10, No. 15, "Access Servers, Dialing Up the LAN," Sep. 10, 1991, pp. 177–277.

J. Salemi, *PC Magazine,* vol. 10, No. 15, "Bulletin Board Software, Tools for Wide–Area Communications," Sep. 10, 1991, pp. 231–300.

M. Stone, *PC Magazine,* vol. 10, No. 15, "E–Mail LAN Links, Gateways to the World," Sep. 10, 1991, pp. 303–345.

F. Derfler & K. Maxwell, *PC Magazine,* vol. 10, No. 15, "Linking LANs the Media Move the Message," Sep. 10, 1991, pp. 351–374.

F. Derfler & K. Maxwelll, *PC Magazine,* vol. 10, No. 15, "Public Data Networks, Reliable Relays," Sep. 10, 1991, pp. 177–227.

P. Stephenson, *LAN Magazine,* "Chip Awat at Viruses," Oct. 1992, pp. 95–102.

*PC Computing,* "Mobile Computing, No–Hassle Solutions for Keeping Files in Sync," Jul. 1993, pp. 218–219.

Advertisement, MicroCom (R), "Carbon Copy, #1 in Remote Control," 1 page.

Advertisement, Symantec, "The Norton pc Anywhere TM, Controlling Your Desktop PC from a Portable Used to Require a Little Training," 1 page.

Microsoft Croporation, *Microsoft MS–DOS(R) 6 Users Guide,* Chapter 7 "Features for Your Laptop Computer, Using Interlink to Connect Two Computers," Copyright 1993, pp. 161–166.

Bershad, "Watchdogs: Extneding the UNIX File System," Feb. 12, 1988, pp. 267–275.

Needham, "Using Encryption for Authentication in Large Networks of Computers," Dec. 1978, pp. 993–999.

COMBINED CALCIUM AND VITAMIN SUPPLEMENTS FOR BONE GROWTH

This is a continuation of application Ser. No. 08/108,151 filed on Aug. 17, 1993 which is continuation of application Ser. No. 07/944,024 filed on Sep. 11, 1992 which is a continuation of application Ser. No. 07/695,823 filed on May 6, 1991, all now abandoned.

TECHNICAL FIELD

The present invention relates to nutritional and therapeutic improvements in calcium supplements containing vitamin D. These supplements are useful for increasing bone growth and treating age-related bone loss. They can be used in conjunction with foods and beverages or taken as an oral solid or liquid supplement. The invention also relates to a method of building bone or treating bone loss in osteoporotic patients, post-menopausal women and/or elderly men.

BACKGROUND OF THE INVENTION

Vitamin and mineral supplements for human and veterinary use are commonplace. Some diets, heavy physical exercise and disease conditions may require the intake of considerable quantities of minerals and vitamins apart from those generally obtained through what otherwise would be considered a normal diet. Calcium and vitamin supplementation is important primarily for those who have inadequate diets, including growing children. Older adults have an additional need for calcium to help prevent the bone loss which occurs as a normal consequence of the aging process. In particular, postmenopausal women need additional calcium due to hormonal changes which can accelerate the bone loss rate leading to a further diminishment in bone mass.

There are well-recognized problems associated with adding both calcium and vitamin D to foods and beverages. Some of these are taste; calcium tends to be chalky in flavor. In addition, the solubility of many calcium sources prevents them from being added to many beverages. Interactions of calcium with the food or beverage affect the stability and/or the bioavailabilty of the product. This invention provides a means for making such product.

This invention also relates to methods of building bone in humans and other animals, i.e., for the treatment of age-related bone loss and related disorders. In particular, this invention relates to such methods of treatment by administration of calcium, citrate and malate ions and vitamin D.

Calcium is the fifth most abundant element in the human body. It plays an important role in many physiological processes, including nerve and muscle functions. Not surprisingly, nutritional and metabolic deficiencies of calcium can have broad-ranging adverse effects. Since about 98% to 99% of the body's calcium is found in bone tissues, many of these adverse effects are manifested through deficiencies in the structure, function and integrity of the skeletal system.

The most common metabolic bone disorder is osteoporosis. Osteoporosis can be generally defined as the reduction in the quantity of bone, either from the reduction in bone formation or the acceleration of bone resorption, in either event the result is a decrease in the amount of skeletal tissue and resultant bone fractures. In general, there are two types of osteoporosis: primary and secondary. "Secondary osteoporosis" is the result of an identifiable disease process or agent. However, approximately 90% of all osteoporosis cases are idiopathic "primary osteoporosis". Such primary osteoporosis includes postmenopausal osteoporosis, age-associated osteoporosis (affecting a majority of individuals over the age of 70 to 80), and idiopathic osteoporosis affecting middle-aged and younger men and women.

For some osteoporotic individuals the loss of bone tissue is sufficiently great so as to cause mechanical failure of the bone structure. Bone fractures often occur, for example, in the wrist, hip and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. Two reactions are involved, bone loss or resorption and bone growth or accretion. This remodeling occurs in a series of discrete pockets of activity in the bone. These pockets are lined with two different cell types called "osteoclasts" and "osteoblasts". Osteoclasts (bone dissolving or resorbing cells) are responsible for the resorption of a portion of bone within the bone matrix, during the resorption process. After resorption, the osteoclasts are followed by the appearance of osteoblasts (bone forming cells), which then refill the resorbed portion with new bone.

In young healthy adults, the rate at which the osteoclasts and osteoblasts are formed maintains a balance of bone resorption and bone formation. However, as a normal consequence of aging an imbalance in this remodeling process develops, resulting in loss of bone at a rate faster than the accretion of bone. As imbalance continues over time the reduction in bone mass and thus bone strength leads to fractures.

Many compositions and methods are described in the medical literature for the "treatment" of osteoporosis. See, for example, R. C. Haynes, Jr. et al., "Agents affecting Calcification", *The Pharmacological Basis of Therapeutics*, 7th Edition (A. G. Gilman, L. S. Goodman et al., Editors, 1985); and G. D. Whedon et al., "An Analysis of Current Concepts and Research Interest in Osteoporosis", *Current Advances in Skeletogenesis* (A. Ornoy et al., Editors, 1985). Estrogen is often used to affect the metabolism of calcium by influencing the osteoblast cells. Treatments using fluoride have also been described. However, the utility of such agents may be limited, because of possible adverse side effects. See W. A. Peck, et al., *Physician's Resource Manual on Osteoporosis* (1987), published by the National Osteoporosis Foundation.

Nutritional therapies for osteoporosis have also been proposed. Many calcium-containing compounds and vitamins compositions have been described for use as nutritional supplements. Many commercial preparations are also available, typically containing calcium carbonate or calcium phosphate. Other calcium salts have also been described for use in calcium supplements, including calcium lactate, calcium citrate and calcium gluconate.

U.S. Pat. No. 3,949,098 issued Bangert (assigned Nabisco, 1976) describes a nutritious orange drink concentrate that contains whey protein. The patent suggests the addition of minor amounts of vitamins, including vitamin D, and other nutrients which include various minerals, such as calcium salts.

U.S. Pat. No. 4,497,800 issued to Larsen et al (assigned Mead Johnson & Company, 1985) describes a nutritionally complete ready-to-use liquid diet for providing total patient nourishment. The diet contains free amino acids and small peptides, a carbohydrate source, and nutritionally significant amounts of all essential vitamins and minerals, and stabilizers. Most of these minerals are given as the gluconate salt. Cholecalciferol ($D_3$) is included.

"Effects of calcium carbonate in hydroxyapatite on zinc and iron retention in postmenopausal women", Dawson-Hughes, Seligson and Hughes, *American Journal of Clinical Nutrition*, 44, 83–88 (1986) describes the effect of calcium carbonate on whole-body retention of zinc and iron in thirteen healthy post menopausal women. The test meal, including both dry food and a formulated beverage, included iron, calcium, copper and zinc at a level of one-third the usual daily requirement. These are levels normally found in human diets.

U.S. Pat. No. 3,992,555 issued to Kovacs (assigned Vitamins, Inc., 1976) describes food supplements prepared by mixing assimilable iron compounds, vitamins and minerals with a heated edible fat carrier. Calcium and vitamin D are among the minerals in the supplement.

U.S. Pat. No. 3,950,547 issued to Lamar et al (assigned Syntex Inc, 1976) describes a dietary composition containing peptides and/or amino acids, lipids and carbohydrates in an aqueous emulsion. Vitamins, including D, are added. Calcium citrate is also used.

U.S. Pat. No. 4,070,488 issued to Davis (unassigned, 1978) discloses a highly stabilized balanced nutritive composition useful in supplementing the diet of humans and/or animals. This composition contains gelatin. The patent discloses that the sulfhydryl groups of the gelatin can render copper inactive toward ascorbic acid.

U.S. Pat. No. 4,214,996 issued to Buddemeyer et al (R.G.B. Laboratories, 1980) discloses mineral compositions which are very soluble. These compositions contain calcium, other minerals and vitamins.

U.S. Pat. No. 4,351,735 to Buddemeyer et al (R.G.B. Laboratories, 1982) is related to the '996 patent.

"Nutrients and Nutrition of Citrus Fruits," *Citrus Nutrition and Quality*, Ting, (American Chemical Society, 1980) discloses the presence of certain trace minerals in orange juice. Calcium and magnesium are the two major divalent cations in orange juice. The levels of all the minerals are low. No vitamin D has been reported in citrus juices.

Milk contains solubilized calcium and is often fortified with vitamin D. Milk's calcium is about 50% calcium citrate and 50% calcium phosphoprotein complexes.

The utility of these known supplements varies. Unlike agents (such as estrogen) which affect the metabolism of bone, calcium nutritional supplements have been thought to merely provide a source for calcium (which may or may not be properly absorbed and metabolized). See, for example, B. Riis et al., "Does Calcium Supplementation Prevent Postmenopausal Bone Loss?," *New England J. of Medicine*, 316, 173–177 (1987); L. Nilas et al., "Calcium Supplementation and Postmenopausal Bone Loss," *British Medical Journal*, 289, 1103–1106 (1984); and H. Spencer et al., "NIH Concensus Conference: Osteoporosis," *Journal of Nutrition*, 116, 316–319 (1986).

It has now been discovered, however, that the administration of mixtures of certain calcium salts, i.e. calcium citrate and malate, and vitamin D are effective for delaying age-related loss of bone. In particular, as compared to nutritional regimens known in the art, these methods afford greater efficacy in the treatment of age-related bone loss and related disorders.

It would be desirable, therefore, to have mixed calcium and vitamin D therapies which are compatible and nutritionally available. It would also be quite useful to have such supplements which could be added to food and beverage compositions without undesirably affecting organoleptic or aesthetic properties.

It is an object of the present invention to provide calcium mineral supplements which, when combined with vitamin D, provide bone growth and can be used to treat age-related bone loss or to correct the imbalance that occurs between bone formation and bone resorption.

It is a further object of this invention to provide foodstuffs, beverages and beverage concentrates which are supplemented with calcium and vitamin D therapies.

These and other objects are readily apparent from the description herein.

SUMMARY OF THE INVENTION

The supplements employ specific calcium salts of mixtures of citric and malic acids combined with vitamin D. Estrogen can be used in conjunction with any of these therapies. These supplements can be added to foods and beverages.

The present invention provides methods for building bone in a human or other animal subject, comprising administering to said subject a safe and effective amount of vitamin D and calcium citrate malate. The calcium citrate malate comprises a complex or a mixture of calcium salts having a ratio of moles of calcium to moles of citrate to moles malate of from about 2:1:1 to about 8:2:1. The combination is preferably administered in foods/beverage application or in a solid dosage form, i.e. a tablet.

It also includes dry beverage mixes and other beverages or beverage syrups. A typical beverage comprises from about 0.06% to about 0.15% calcium, citric and malic acids wherein the molar weight ratio of calcium to citric to malic acids is preferably from 4:2:3 to 6:2:3, from about 0.25 to about 25 micrograms of vitamin D, depending on the vitamin D source, per serving and flavor and sweetener.

All ratios, proportions and percentages herein are by weight, unless otherwise specified. All weights of calcium are on an elemental basis unless otherwise specified.

DETAILED DESCRIPTION OF THE INVENTION

The present invention relates to stable calcium and vitamin D supplements and supplemented foods and beverages including dry beverage mixes and to a method of building bone.

As used herein, the term "comprising" means various components can be conjointly employed in the calcium and vitamin D supplements, foods and beverages of the present invention. Accordingly, the terms "consisting essentially of" and "consisting of" are embodied in the term comprising.

By "nutritional" or "nutritionally-supplemental amount" herein is meant that the mineral and vitamin sources used in the practice of this invention provide a nourishing amount of vitamin D and calcium. This is supplemental or in addition to the amount found in the average diet. This supplemental amount will comprise at least 25% of the Recommended Dietary Allowance (RDA) of the daily intake of calcium and vitamin D. Preferably, at least 50% of the Recommended Dietary Allowance (RDA) will be provided. The RDA for vitamin and minerals is as defined in The United States of America (see Recommended Daily Dietary Allowance-Food and Nutrition Board, National Academy of Sciences-National Research Council).

Specific compounds and compositions to be used in these processes must, accordingly, be pharmaceutically acceptable. As used herein, a "pharmaceutically acceptable" component is one that is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will vary with such factors as the particular condition being treated, the physical condition of the patient, the duration of the treatment, the nature of concurrent therapy (if any), and the specific formulations employed.

As used herein, the term "flavors" includes both fruit and botanical flavors.

As used herein the term "sweeteners" includes sugars, for example, glucose, sucrose, and fructose. Sugars also include high fructose corn syrup solids, invert sugar, sugar alcohols, including sorbitol, and mixtures thereof. Artificial sweeteners are also included in the term sweetener.

Vitamin D

Vitamin D includes vitamin D, cholecalciferol ($D_3$), ergocalciferol ($D_2$) and its biologically active metabolites and precursors such as, $1\alpha$, $25\text{-}(OH)_2$ vitamin D; 25 OH vitamin D, its biological precursor; and $1\alpha$ hydroxy vitamin D, and analogues of the dihydroxy compound. These materials promote intestinal absorption of calcium, contribute to plasma calcium regulation by acting on the remodeling processes of accretion and resorption and stimulate reabsorption of calcium by the kidney.

Biological active vitamin D metabolites and precursors like those defined above possess more biopotency than vitamin $D_2$ or $D_3$. Thus, the amount required to be safe, effective and nourishing is less and will generally comprise from about 0.25 to about 15.0 micrograms per serving or unit dose. Vitamin $D_3$ and $D_2$ is preferably present at about 0.6 to about 25 micrograms.

Estrogen

Estrogen therapy can be used along with any of these regimens. The method herein also comprises coadministering from about 0.3 mg to about 6 mg of estrogen along with the calcium and vitamin D, and/or calcium and vitamin D along with calcitonin or etidronate (or diphosphonates). Preferably from 0.625 mg to about 1.25 mg of estrogen is taken daily. Any viable estrogen hormone replacement can be used.

Calcium Component

In supplements of the type disclosed herein, the nutritionally supplemental amount for calcium will generally comprise more than 50% of the RDA and preferably 80% to 100% RDA per unit portion of the finished supplement. Of course, it is recognized that the preferred daily intake of any mineral may vary with the user.

In general, the RDA (calcium) will range from 360 mg per 6 Kg (body weight) for infants to 800 mg/54–58 Kg female, depending somewhat on age. Moreover, it can be difficult to supplement beverages with more than 20–30% RDA of calcium (based per serving) without encountering precipitation and/or organoleptic problems. However, this level of supplementation is equivalent to cow's milk in calcium value, and is therefore acceptable.

It is essential to this supplementation that the calcium salts be soluble. This solubilization aids in making the calcium more readily bioavailable. It is equally important that both the calcium and vitamin D be bioavailable. To add this the ingredients should be solubilized and absorbed by the stomach and or intestine. Any excipients used should disintegrate easily so that the calcium and vitamin D are released. The choice of calcium salts and vitamin D depends upon the interaction of the salts in acid (stomach pH) solutions or basic (intestinal pH) solutions.

Solubility also plays an important role in the preparation of foods and beverages containing these supplements.

Calcium Citrate Malate Compositions

The methods of this invention involve administration of a mixture of calcium salts, herein "calcium citrate malate," comprising calcium salts of citric acid and malic acid. The calcium citrate malate may consist of a mixture of calcium citrate and calcium malate, a complex of calcium containing citrate and malate ligands, a mixture of a calcium salt with citric acid and malic acid, or combinations thereof. Mixtures of a calcium salts and citric and malic acids may be used to form calcium citrate malate in situ, the beverage. Preferred are calcium citrate malate mixtures made by adding calcium carbonate, calcium hydroxide or other suitable source to a mixture of citric and malic acids.

The molar ratio of citrate in the salt is from 1 to 3 and the molar ratio of malate from about 1 to 5. The molar ratio of calcium is from 2 to 8. The ratio of total moles calcium:total moles citrate:total moles of malate is from about 2:1:1 to about 8:2:1, preferably from about 4:2:3 to about 6:3:4. The calcium citrate malate may contain other acid anions in addition to citrate and malate. Such anions may include, for example, carbonate, hydroxide, phosphate and mixtures thereof depending on the calcium source.

Preferably, the calcium citrate malate is neutral, comprised entirely of citrate and malate anions. Thus, preferably, the equivalents of calcium (2×moles calcium) is about equal to the total number of equivalents of citrate (3×moles citrate) plus malate (2×moles malate). A preferred calcium citrate malate has a calcium:citrate:malate molar composition of about 6:2:3 and 4:2:3.

The calcium citrate malate used in the methods of this invention may be provided in solid or liquid forms. Calcium citrate malate for use in solid forms may be made, for example, by first dissolving citric acid and malic acid, in the desired molar ratio, in water. Calcium carbonate may then be added to the solution, in such amount that the ratio of moles calcium to moles citrate and moles malate is as desired. Carbon dioxide will be evolved. The solution may then be dried (as by freeze drying or oven drying at temperatures below 100° C.) to obtain the calcium citrate malate. Methods for making calcium citrate malate are described in the following documents: Japanese Patent Specification SHO 56-97248, Kawai, published Aug. 5, 1981; and in U.S. Pat. No. 4,722,847 issued to Heckert (1988). Co-pending application of Fox et al, Ser. No. 07/537,313 filed Jun. 14, 1990; Japanese Patent Specification SHO 56-97248, Kawai, published Aug. 5, 1981; and in U.S. Pat. No. 4,722,847 issued to Heckert (1988).

Calcium carbonate can be used as the calcium source for making the calcium citrate malate. Other sources include calcium oxide and calcium hydroxide. Calcium chloride, calcium phosphate and calcium sulphate can be used, but they are not preferred since the anions make an acid solution, i.e. hydrochloric acid, sulfuric and phosphoric acid, respectively, which can adversely affect the flavor of beverages and foods containing the calcium citrate malate.

A solid forms during the mixing of the calcium oxide or calcium hydroxide with the citric and malic acid. When these materials are used, it is necessary to mix the solution until all of the calcium appears to have dissolved. The calcium citrate malate ligand will precipitate when its solubility is exceeded.

The preferred method of preparation is to prepare a highly concentrated solution of the calcium citrate malate which quickly and efficiently forces metastable calcium citrate malate out of solution. Concentrations of from 20% to 75% are preferred. Preferably the concentration is from 40% to 65%.

The reaction temperature can be ambient (20° C.) or higher. Preferably the temperature of the reaction is in the range of 30° C. to 80° C. Most preferably it is from 40° C. to 60° C.

Flavor Component

The flavor component of the present invention contains flavors selected from natural flavors, botanical flavors and mixtures thereof. The term "fruit flavors" refers to those flavors derived from the edible reproductive part of a seed plant, especially one having a sweet pulp associated with the seed. Also included within the term "fruit flavor" are synthetically prepared flavors made to simulate fruit flavors derived from natural sources.

The term "botanical flavor" refers to flavors derived from parts of a plant other than the fruit; i.e. derived from bean, nuts, bark, roots and leaves. Also included within the term "botanical flavor" are synthetically prepared flavors made to simulate botanical flavors derived from natural sources. Examples of such flavors include cocoa, chocolate, vanilla, coffee, kola, tea, and the like. Botanical flavors can be derived from natural sources such as essential oils and extracts, or can be synthetically prepared.

The particular amount of the flavor component effective for imparting flavor characteristics to the supplements and food or beverage mixes of the present invention ("flavor enhancing") can depend upon the flavor(s) selected, the flavor impression desired, and the form of the flavor component. The flavor component can comprise at least 0.05% by weight of the beverage composition and preferably from 0.05% to about 10%. The amount of flavor added to the food, beverage or supplement is within the skill of one in the art and depends on the flavor intensity desired.

For chocolate or cocoa, the amount of flavor added is from about 0.05% to about 20%. Lower levels of artificial or synthetic chocolate flavors are used than for cocoa itself.

Beverages can be flavored with fruit or other botanical flavors, e.g., vanilla, strawberry, cherry, pineapple, banana, and mixtures thereof.

The calcium, citric and malic acids can be added with the vitamin D to a 100% fruit juice or a diluted fruit juice. The sugars present in the juice are useful sweeteners, and the juice can be the flavor component. Such beverages can contain from 5% to 100% juice. Preferably dilute juice beverages will have from 10% to 40% juice. Preferred juices for 100% juice products or diluted products are orange, cranberry, apple, pear, grape, raspberry, lemon, grapefruit, pineapple, banana, blackberry, blueberry and passion fruit juices and mixtures thereof.

Sweetener Component

The sweetener composition is usually a monosaccharide or a disaccharide. These include sucrose, fructose, dextrose, maltose and lactose, but other carbohydrates can be used if less sweetness is desired. Mixtures of sugars can be used also.

Other natural or artificial sweeteners can be used. These include saccharin, cyclamates, acetosulfam, L-aspartyl-L-phenylalanine lower alkyl ester sweeteners (e.g. aspartame), L-aspartyl-D-alanine amides disclosed in U.S. Pat. No. 4,411,925 to Brennan et al., issued Oct. 23, 1983, L-aspartyl-D-serine amides disclosed in U.S. Pat. No. 4,399,163 at Brennan et al., issued Aug. 16, 1983, L-aspartyl-L-1-hydroxymethyl-alkaneamide sweeteners disclosed in U.S. Pat. No. 4,338,346 to Brand, issued Dec. 21, 1982, L-aspartyl-1-hydroxyethyl-alkaneamide sweeteners disclosed in U.S. Pat. No. 4,423,029 to Rizzi, issued Dec. 27, 1983, L-aspartyl-D-phenylglycine ester and amide sweeteners disclosed in European Patent Application 168,112 to J. M. Janusz, published Jan. 15, 1986, and the like. A particularly preferred sweetener is aspartame.

The amount of the sweetener effective in the food, beverage, mixes or supplements of the invention depends upon the particular sweetener used and the sweetness intensity desired. For noncaloric sweeteners, the amount varies depending upon the sweetness intensity of the particular sweetener (from about 0.5% to 2%). For sucrose, this amount can be from 10% to 85% (typically from 55% to 70%) by weight. In determining the amount of sugar, any sugar or other sweetener present in the flavor component or juice is also included. Low-calorie sweetener combinations containing a noncaloric sweetener such as aspartame and a sugar, such as corn syrup solids, or sugar alcohols can also be used in beverage mixes. In general, the amount of sweetener will be from about 0.5% to about 85%.

Other Ingredients

Other minor ingredients are frequently included in supplements, foods and beverages. Such ingredients include preservatives such as benzoic acid and salts thereof, sulfur dioxide, butylated hydroxyanisole, butylated hydroxytoluene, etc. Also, typically included are colors derived either from natural sources or synthetically prepared.

Salt, e.g. sodium chloride, and other flavor enhancers can be used to improve the flavor of the food, beverage or supplement.

Emulsifiers can also be included. Any food grade emulsifier can be used. Lecithin is a preferred emulsifier. Other edible emulsifiers include mono- and diglycerides of long chain fatty acids, preferably saturated fatty acids, and most preferably, stearic and palmitic acid mono- and diglycerides. Propylene glycol esters are also useful in beverage mixes.

Fats or oils can also be added to supplements or foods to make them more palatable. Since vitamin D is fat soluble, minor amounts of fat can be used to solublize the vitamin 0. Dry milk solids can also be included to make a dry, synthetic, flavored milk or chocolate milk type beverage.

pH and Other Beverage Ingredients

The pH of the beverages and beverage concentrates of the present invention is dependent upon the weight ratios of the acids, the total amount of acids and the sourness impression desired. Typically, the pH can range from 2.5 to 6.5. Preferred carbonated beverages have a pH of from 3.0 to 4.5.

Other minor beverage ingredients are frequently included in beverages and concentrates. Also, typically included are colors derived either from natural sources or synthetically prepared. See L. F. Green, *Developments in Soft Drinks Technology*, Vol. 1 (Applied Science Publishers Ltd. 1978), pp. 185–186 (herein incorporated by reference) for preservatives and colors used in beverages.

Beverage Preparation

The beverages and concentrates of the present invention can be prepared by standard beverage formulation techniques. It should be understood, however, that carbonated beverage making techniques, when appropriately modified, are also applicable to noncarbonated beverages. Also, while the following description is with reference to sugar containing beverages, diet beverages containing noncaloric sweeteners can also be prepared by appropriate modification. Beverages can include dry beverage mixes which are made by mixing flavors, sweeteners, and other optional ingredients as well as fruit juices and dilute fruit juices.

In making a sugar sweetened carbonated beverage, a beverage concentrate is usually formed containing from 30 to 70% by weight water. This beverage concentrate typically contains the emulsified or water-soluble flavors, emulsion stabilizing agents, and weighting agents if needed, any color desired and suitable preservatives. After the concentrate is formed, sugar and water are then added to make a beverage syrup. This beverage syrup is then mixed with an appropriate quantity of water to form the finished beverage. The weight ratio of water:syrup is from about 3:1 (3× syrup) to about 5:1 (5× syrup). To make a carbonated beverage carbon dioxide can be introduced either into the water mixed with the beverage syrup or into the drinkable diluted beverage to achieve carbonation. The beverage can be sealed in a container such as a bottle or can. See L. F. Green, *Developments in Soft Drinks Technology*, Vol. 1, (Applied Science Publishers Ltd. 1978), pp. 102–107 (herein incorporated by reference), for a further description of beverage making, in particular the process for carbonation.

The amount of carbon dioxide in the beverage depends upon the particular flavor system used and the amount of carbonation desired. Usually, carbonated beverages of the present invention contain from 1.0 to 4.5 volumes of carbon dioxide. Preferred carbonated beverages contain from 2 to 3.5 volumes of carbon dioxide.

The calcium source and the acids (citric, malic, phosphoric) can be added at various points in these processes. The calcium source and acids are preferably added at the same point in this process, but can also be added at different points. Usually, the calcium source and acids are included during preparation of the beverage concentrate or beverage syrup. Preferably the vitamin D is added after the calcium and acid source have been mixed in. It can be added with the oil flavors or weighting oil.

When making a dry beverage, it is preferred to mix a powdered calcium citrate malate powder with the sugar or artificial sweeteners, vitamin D and flavors. Colors and colored coated sugars can be added. Dry chocolate milk beverages are preferred dry beverage mixes. These can be diluted either with water or milk. Milk provides additional vitamin D and calcium citrate. A typical formula for chocolate mixes is:

a) from 0% to 25% milk solids, preferably from 5% to 20% non-fat milk solids;

b) from 0.05% to 20% flavor, preferably cocoa;

c) from about 0.5 to about 85% sweetener, preferably sucrose; and d) from about 0.6% to about 0.15% calcium citrate malate and from about 0.60 to about 30 micrograms vitamin D.

Supplement Forms

Solid forms include tablets, capsules, granules and bulk powders. Tablets may contain suitable binders, lubricants, diluents, disintegrating agents, coloring agents, flavoring agents, flow-inducing agents and melting agents. Liquid oral dosage forms include aqueous solutions, emulsions, suspensions, solutions and/or suspensions reconstituted from non-effervescent granules and effervescent preparations reconstituted from effervescent granules. Such liquid oral dosage forms may contain, for example, suitable solvents, preservatives, emulsifying agents, suspending agents, diluents, sweeteners, melting agents, and coloring and flavoring agents. A preferred liquid dosage form contains calcium citrate malate and vitamin D in a juice-containing beverage or other beverage.

The calcium citrate malate and vitamin D therapy can be coadministered in one tablet, liquid, food or beverage or they can be administered separately. A tablet or capsule containing the vitamin D and a second tablet with the calcium citrate malate are easy to formulate and to swallow. Vitamin D could also be coadministered with a calcium citrate malate containing beverage.

Specific examples of pharmaceutically acceptable carriers and excipients that may be used to formulate oral dosage forms of the present invention are described in U.S. Pat. No. 3,903,297, Robert, issued Sep. 2, 1975 Techniques and compositions for making dosage forms useful in the methods of this invention are described in the following references; 7 *Modern Pharmaceutics*, Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition. (1976).

Method of Building Bone

Various oral dosage forms of calcium citrate malate and vitamin D may be used in the present invention. Such dosage forms comprise a safe and effective amount of calcium citrate malate, vitamin D and a pharmaceutically acceptable carrier. Preferably the pharmaceutically acceptable carrier is present at a level of from about 0.1% to about 99%, preferably from about 0.1% to about 75%, by weight of the composition. Unit dosage forms (i.e., dosage forms containing an amount of calcium citrate malate suitable for administration in one single dose, according to sound medical practice) preferably contain from about 100 mg to about 1000 mg, preferably from about 100 mg to about 500 mg, more preferably from about 200 mg to about 300 mg of calcium (on an elemental basis).

Preferably, from about 175 milligrams to about 2000 milligrams of calcium (as elemental calcium) are administered to said subject, per day. More preferably, from about 250 milligrams to about 1500 milligrams, most preferably from about 350 milligrams to about 1000 milligrams, of calcium are administered, per day. The specific amount of calcium citrate malate to be administered depends upon the relative percentage weight of calcium in the particular calcium citrate malate employed.

The recommended daily allowance for vitamin D ranges from about 200 IU to 400 IU depending upon age. The supplements used herein have a unit dosage amount of from 25 IU to 800 IU or from about 0.60 to 20 micrograms per serving. Up to 30 micrograms can be used. An IU of vitamin D is 0.025 micrograms.

Specifically, the present invention provides a method for building bone in a human or other animal subject, comprising administering to said subject a safe and effective amount of calcium citrate malate and vitamin D for a period of time sufficient to achieve an increase in the net skeletal mass of said subject. As used herein, "building bone" refers to a decrease in the net skeletal loss of bone of the subject treated and therefore a net skeletal increase in mass. The slowing of the rate of bone loss and the increase in growth rate occur simultaneously so the net bone density may stay the same. The increase in mass may be at any skeletal site, including spine, hip, long bones of arms or legs or in the skeleton as whole. Preferably, the net skeletal mass is increased by at least about 0.1%, more preferably at least about 1%.

The loss of bone is cumulative over a long period of time. Typically, lifetime loss in bone mass is about 35% in males and 50% in females. Thus, even though a net skeletal increase of as little as 0.5% in one year is not particularly critical, over 10 years this results in 5% more bone mass than would be present if bone loss continued at its usual rate.

"Administering" refers to any method which, in sound medical practice, delivers the vitamin D and calcium citrate malate used in this invention to the subject to be treated in such a manner so as to be effective in the building of bone.

The specific period of time sufficient to achieve an increase in the net skeletal mass of the subject may depend on a variety of factors. Such factors include, for example, the specific mineral formulation employed, the amount of minerals administered, the age and sex of the subject, the specific disorder to be treated, concomitant therapies employed (if any), the general physical health of the subject (including the presence of other disorders), the extent of bone loss in the individual, and the nutritional habits of the individual. Although the administration of even small quantities of calcium citrate malate and vitamin D may build bone, the net increase in bone mass may not be detectable for short periods of administration.

For the treatment of age-related bone loss, the calcium citrate malate and vitamin D are administered for at least about six months, preferably for at least about twelve months. Of course, such administration may be continued indefinitely, according to sound medical practice.

The methods of this invention may be employed in the treatment of any of a variety of disorders in which the building of bone is desired. Thus, preferably, the human or other animal "subject" of the methods of this invention is in need of a method for building bone, i.e., the subject has a disorder for which building of bone or decrease in rate of bone resorption would be advantageous according to sound medical practice. Such disorders include, for example, bone fractures, reduced mass and disorders typified by bone loss, such as age-related bone loss and osteoporosis (both primary and secondary forms).

A preferred method of this invention is for the treatment of age-related bone loss.

In addition to estrogen therapy, other therapies can be used along with the calcium and vitamin D supplements of this invention. Preferred therapies include the administration of calcitonin or etidronate or other diphosphonates and aminodiphosphonates to the human subject.

The following example illustrates compositions of the type provided by the practice of this invention, but is not intended to be limiting thereof.

Example I

About 240 post-menopausal women are treated by administering a composition containing calcium citrate malate having a molar calcium:citrate:malate composition of about 6:2:3. The calcium citrate malate is made by first dissolving approximately 384.2 grams of citric acid and approximately 402.3 grams of malic acid in approximately 2 liters of water. This citrate/malate solution is then heated to approximately 55° C. (131° F.), with stirring. Separately, approximately 600.6 grams of calcium carbonate is added to approximately 1.2 liters of water, forming a slurry, with stirring.

The citrate/malate solution is then removed from its heat source, and the calcium carbonate slurry is added slowly, with stirring. The rate of addition is controlled, to contain the reaction as carbon dioxide is released. An additional quantity of water, approximately 0.4 liters, is finally added. The reaction mixture is then stirred for approximately 1 to 1.5 hours. The reaction is essentially complete as the pH of the solution equilibrates to approximately 4.3.

A precipitate of calcium citrate malate is thus formed. The excess reaction liquid is filtered off. The calcium citrate malate is dried, for approximately 12 hours at approximately 105° C. (221° F.), reducing the moisture level to less than about 1%. The dried product is then milled to approximately 10–20 mesh size, for a swallowable tablet formulation. Each tablet contains 250 mg.

The swallowable tablet dosage form is then made, comprising:

| Component | % (By Weight) |
|---|---|
| Calcium citrate malate* | 99.73 |
| Magnesium stearate | 0.27 |

*Having a molar calcium:citrate:malate composition of approximately 6:2:3, made as described above is this example.

The tablet formulation is made by thoroughly admixing the powders, and tabletting using a standard tablet press, to form tablets weighing approximately 1104 milligrams. The tablets are then coated, using a pan coater. The coating solution contains approximately 11% hydroxypropylmethyl cellulose, approximately 2% polyethylene glycol, approximately 3.5% colorant, and the balance of water.

One half of the women receive a supplement containing 400 IU of vitamin D while the other half receive a placebo. The vitamin D supplement and placebo contain 127 mg of calcium as calcium phosphate. All the women received 250 mg calcium as calcium citrate malate.

At the beginning of the study and after one year the bone density of the spine and overall body bone density are measured by dual x-ray absorptiometry.

| Percent Change in Bone Density After 1 Year | | |
|---|---|---|
| | Spine | Whole Body |
| CCM + Placebo | 0.15 ± 0.25 | −0.08 ± 0.11 |
| CCM + Vitamin D | 0.85 ± 0.23 | 0.03 ± 0.12 |

The change in the bone density of the spine is statistically significant and shows a net increase in bone density. The whole body bone density is not significantly different. While this means there was no gain in the whole body bone density, it also means that the women did not lose bone density over the year which is expected in normal post-menopausal women not taking calcium supplements. The CCM/placebo patients also did not lose bone in the spine or whole body, but they did not gain bone as did those taking vitamin D.

What is claimed is:

1. A method for building of bone in a human subject suffering from age-related bone loss comprising administering to said subject synergistic effective amounts of a mineral supplement comprising calcium citrate malate (CCM) and vitamin $D_3$ for a sufficient period of time to increase the net skeletal mass of said subject by at least about 0.1%, wherein said calcium citrate malate is administered at a level from about 175 milligrams to about 2000 milligrams (on an elemental calcium basis) and wherein vitamin $D_3$ is administered at a level of from 0.60 to 30 micrograms per day.

2. A method for building bone according to claim 1 wherein said calcium citrate malate is administered at a level of from about 250 to 1500 milligrams (on an elemental calcium basis), and wherein said vitamin $D_3$ is administered at a level of from 2.5 to 25 micrograms per day.

3. A method for building of bone according to claim 2, wherein said period of time is at least about six months.

4. A method for building of bone according to claim 3, wherein said calcium citrate malate has a molar ratio of from about 2:1:1 to about 8:2:1.

5. A method for building of bone according to claim 1, wherein said mineral supplement is in a solid dosage form.

6. A method for building of bone according to claim 1, wherein said mineral supplement is in a liquid dosage form.

7. A method for building of bone according to claim 1, wherein said mineral supplement is administered as a beverage.

8. A method according to claim 7 wherein said beverage contains juice.

9. A method for the building of bone according to claim 1, wherein said period of time is sufficient to increase the net skeletal mass of said subject by at least about 0.5%.

10. A method according to claim 8 wherein said juice is selected from the group consisting of orange juice, apple juice, pear juice, grape juice and cranberry juice.

11. A method according to claim 5 wherein said solid dosage form comprises a tablet or capsule of calcium citrate malate and vitamin $D_3$.

12. A method according to claim 4 wherein said mineral supplement is added to dry beverage mixes.

13. A method of reducing fracture risk according to claim 1, in a human subject suffering from age-related bone loss comprising administering to said subject synergistic effective amounts of a supplement comprising calcium citrate malate and vitamin $D_3$ for a sufficient period of time to increase the net skeletal mass of said subject by at least about 0.1%.

14. A method for reducing fracture risk according to claim 13, wherein said calcium citrate malate is administered at a level of from about 173 milligrams to about 2000 milligrams (on an elemental calcium basis), and wherein said vitamin $D_3$ is administered at a level of from 0.60 to 30 micrograms per day.

15. A method for reducing fracture risk according to claim 13, wherein said calcium citrate rmalate has a molar ratio of from about 2:1:1 to about 8:2:1.

16. A mineral supplement for building bones comprising synergistic effective amounts of:
   a) from 100 to 1000 mg of calcium (on an elemental basis) in the form of carboxylate selected from the group consisting of citrate, malate, lactate and mixtures thereof; and
   b) from 0.60 to 25 micrograms of vitamin $D_3$.

17. A supplement according to claim 16 wherein the molar ratio of calcium:citrate:malate is from 2:1:1 to 8:1:1.

18. A supplement according to claim 17 wherein the molar ratio of calcium:citrate:malate is from 4:2:3 to 6:2:3.

19. A supplement according to claim 16 wherein the mineral supplement is an effervescent form.

20. A beverage which comprises
   a) a flavor component which contains a flavor selected from the group consisting of fruit flavors, botanical flavors and mixtures thereof in an amount effective to impart flavor characteristics to the drinkable beverage;
   b) from 30% to 70% by weight sugar; and
   c) synergistic effective amounts of 0.06% to about 0.15% by weight solubilized calcium and from 0.6 to 20 micrograms vitamin $D_3$ wherein said calcium is calcium:citrate: malate comprising from about 0.24% to about 1.05% by weight of an acid component selected from mixtures of citric acid and malic acid; and wherein the calcium, citrate and malate has a weight ratio of moles calcium to moles of citrate to moles of malate in the range of from 2:1:1 to 8:2:1.

21. The beverage of claim 20 wherein said calcium, citrate and malate have a weight ratio of 4:2:3 to 6:2:3 and wherein said beverage comprises from about 0.6 to about 4 micrograms of vitamin $D_3$.

22. The beverage of claim 21 wherein said sweetener comprises from about 6% to 14% by weight sugar.

23. The beverage of claim 22 wherein said sugar is high fructose corn syrup.

24. The beverage of claim 21 wherein said sweetener comprises a non caloric sweetener.

25. A beverage according to claim 21 wherein said flavor is from 10% to 100% fruit juice.

26. A beverage according to claim 20 which comprises a dry mixture of:
   a) from 0% to 25% milk solids;
   b) from about 0.5% to about 25% flavor;
   c) from about 0.5% to about 85% sweetener; and
   d) from about 0.6% to about 0.15% solubilized calcium wherein the moles of calcium to moles of citrate to moles of malate is from 4:2:3 to 6:2:3.

27. A beverage concentrate in liquid form for preparing a drinkable beverage which comprises a) a flavor component which contains a flavor selected from the group consisting of fruit flavors, botanical flavors and mixtures thereof in an amount effective to impart flavor characteristics to the drinkable beverage;
   b) from 30% to 70% by weight sugar; and
   c) synergistic effective amounts of from 0.15% to about 0.5% by weight calcium and from 0.6 to 20 micrograms vitamin $D_3$ wherein said calcium is calcium:citrate:malate comprising from about 0.5% to about 3.5% citric and malic acids and wherein the calcium, citrate and malate has a weight ratio of moles calcium to moles of citrate to moles of malate of from 2:1:1 to 8:1:1.

28. A beverage concentrate according to claim 27 which is a fruit juice concentrate.

* * * * *